United States Patent [19]

Yano et al.

[11] Patent Number: 5,505,936
[45] Date of Patent: Apr. 9, 1996

[54] PHOSPHORIC DIESTERS WHICH ABSORB UV RAYS, METHOD OF PREPARING THE SAME, AND COSMETIC COMPOSITIONS CONTAINING THE SAME

[75] Inventors: Shinji Yano, Naga; Munehisa Okutsu, Wakayama; Katsumi Kita, Izumisano; Yoshiaki Fujikura, Utsunomiya; Junichi Fukasawa, Yokohama, all of Japan

[73] Assignee: Kao Corporation, Tokyo, Japan

[21] Appl. No.: 260,310

[22] Filed: Jun. 15, 1994

[30] Foreign Application Priority Data

Jun. 15, 1993 [JP] Japan ..................... 5-143890

[51] Int. Cl.$^6$ ..................... A61K 7/42
[52] U.S. Cl. ............... 424/60; 514/844; 558/174; 558/179; 558/182
[58] Field of Search ............ 424/59, 60; 514/844

[56] References Cited

U.S. PATENT DOCUMENTS

| | | | |
|---|---|---|---|
| 4,670,575 | 6/1987 | Kurosaki | 558/146 |
| 4,736,051 | 4/1988 | Wakatsuki | 558/105 |
| 5,260,051 | 11/1993 | Cho | 424/57 |

*Primary Examiner*—C. Warren Ivy
*Assistant Examiner*—Evelyn Huang
*Attorney, Agent, or Firm*—Oblon, Spivak, McClelland, Maier, & Neustadt

[57] ABSTRACT

Phosphoric diesters having formula (1):

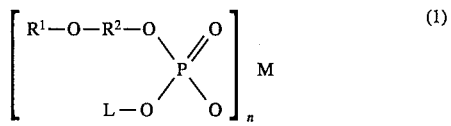

wherein $R^1$ is an acyl group having at least one phenyl group; $R^2$ is a $C_{2-12}$ linear or branched alkylene group which may optionally be inserted with an oxygen atom between carbon atoms thereof; L is a $C_{2-40}$ linear or branched alkyl group which may optionally be inserted with an oxygen atom between carbon atoms thereof or the group $R^1$-O-$R^2$; M is a hydrogen atom, an alkali metal ion, a metal ion of di- or higher valence, an ammonium group, an alkanolammonium group having 2 to 14 carbon atoms, $C_{1-14}$ alkylammonium group; and n is the valence of M are useful UV absorbing compounds. The phosphoric diesters remain on the skin for long periods of time and exhibit lasting UV shielding effects. The compounds and the cosmetic compositions containing the compounds are very safe to the skin.

19 Claims, 1 Drawing Sheet

PHOSPHORIC DIESTERS WHICH ABSORB UV RAYS, METHOD OF PREPARING THE SAME, AND COSMETIC COMPOSITIONS CONTAINING THE SAME

BACKGROUND OF THE INVENTION

1. Field of the Invention

The present invention relates to a phosphoric diester which has a UV (ultraviolet) rays absorbing group and which is useful as an active component of anti-suntan or anti-sunburn cosmetic compositions, a method of preparing the phosphoric diester, and cosmetic compositions containing the phosphoric diester.

2. Description of the Background

Recently, it has been found that ultraviolet rays are deeply involved in the mechanism of the onset of skin diseases such as skin cancer, suntan/sunburn, and aging of the skin. The increase in UV dose caused by the destruction of the ozone layer, which has now become a controversial issue, raises the problem of the possibility of harm by ultraviolet rays.

In view of the foregoing, protecting the skin from UV rays is desired, and accordingly, various cosmetic compositions such as anti-sunburn compositions, skin-care compositions, foundations and similar compositions which contain UV shielding substances have been put on the market.

Ultraviolet rays are divided into three groups: long-wavelength UV rays (UV-A; 320 to 400 nm), medium-wavelength UV rays (UV-B; 290 to 320 nm) and short-wavelength ultraviolet rays (UV-C; up to 290 nm). Among these, UV-A and UV-B both of which reach the surface of the earth have been found to be harmful to the skin. In order to protect the skin from these harmful UV rays, many UV shielding substances have been developed.

For example, inorganic compounds such as titanium oxide, iron oxide and zinc oxide, and oil-soluble organic compounds such as 4-t-butyl-4'-methoxydibenzoylmethane are known as UV-A shielding substances. Substances known to provide shielding from UV-B include p-aminobenzoic acid, salicylic acid, methoxycinnamic acid, and benzophenone derivatives. They are processed in various manners for enhancing the UV-shielding property or for providing a suitable material useful as cosmetic compositions. For example, the former are made into fine particles or ultrafine particles, subjected to hydrophobic surface treatment, or combined with other substances, and the latter are made into derivatives such as metal salts.

In processing to enhance UV-absorbing effects, safety to the skin and retention on the skin for long periods are especially important.

With regard, to safety, consideration must be given not only to the skin-irritating effect of the UV absorbing agent itself but also to irritation of the skin caused when the UV absorbing agent absorbs light. In order to solve this problem, an attempt has been made to avoid direct contact of the UV absorbing agent with the skin while the UV shielding effect of the agent is retained. For example, Japanese Patent Application Laid-open (Kokai) Nos. SHO 62-181213 (1987) and SHO 60-81124 (1985) disclose a method of intercalating UV absorbing agents into clay minerals such as montmorillonite. According to this process, the safety of the agent to the skin can be enhanced by inserting UV absorbing agents into interlayers of clay minerals. However, this process is accompanied by the drawback that the intercalated UV absorbing agent is exchanged with molecules of oils or surfactants if a UV absorbing agent is blended with oils or is incorporated in an emulsion system, causing exuding of the UV absorbing agent and allowing contact of the agent with the skin.

Concerning the retention of UV absorbing agents on the skin, especially organic types involve the problem that their UV-absorbing effect does not last long because they are easily removed by perspiration or by secretion of sebum. In order to solve this problem, Japanese Patent Application Laid-open (Kokai) No. SHO 60-130655 (1985) discloses a technique in which powder particles are coated with UV absorbing agents which have been made into the form of water-insoluble metal salts. In this case, however, the UV shielding effect of the particles coated with UV absorbing agents is not necessarily satisfactory. When a better effect is desired, the quantity of powder particles must be increased, but this in turn leads to deterioration of feel upon use by giving a frictional sensation or lack of proper moistness.

Japanese Patent Application Laid-open (Kokai) No. HEI 2-251240 (1990) discloses a technique in which UV absorbing agents are encapsulated in microcapsules by the use of suitable microcapsulating agents. This involves the drawbacks that highly safe substances admitted for use with cosmetic compositions must be used as a microcapsulating agent, and that thickness and shape of microcapsules must be controlled so as not to decrease the UV shielding effect, which is technically difficult to meet.

Accordingly, UV absorbing agents which are very safe to the skin, which are retained on the skin for long periods and are capable of providing a long-term UV absorbing effect are still desired.

Under the above circumstances, the present inventors carried out extensive studies in an attempt to obtain a UV absorbing agent which is safe and has lasting effects, and as a result, have succeeded in introducing a UV absorbing group into phosphoric diesters known as very safe, and also have found that the thus processed phosphoric diesters form, together with various oils and other organic oil-based UV absorbers, an excellent thixotropic gel which is very useful as a UV absorbing agent when used as an ingredient of cosmetic compositions due to its safety to the skin, retainability on the skin and lasting ability of holding the oil-based UV absorbers. The present invention was accomplished based on these findings.

SUMMARY OF THE INVENTION

One object of the present invention is to provide phosphoric diesters represented by formula (1):

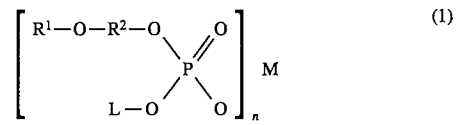

wherein $R^1$ is an acyl group having at least one phenyl group, $R^2$ is a $C_2$ to $C_{12}$ linear or branched alkylene group which may optionally have an oxygen atom inserted between carbon atoms thereof, L is a $C_2$ to $C_{40}$ linear or branched alkyl group which may optionally have an oxygen atom inserted between carbon atoms thereof or a group $R^1$-O-$R^2$-, M is a hydrogen atom, an alkali metal ion, a metal ion of di- or higher valence, an ammonium group, an alkanolammonium group wherein the alkanol has 2 to 14 carbon atoms, an alkylammonium group having 1 to 14 carbon atoms, and n is the valence of M; cosmetic compositions containing the phosphoric diesters and a method of preparing the phosphoric diesters.

Another object of the present invention is to provide a method of preparing the phosphoric diesters.

A further object of the invention is to provide a cosmetic compositions containing the phosphoric diesters.

The above and other objects, features and advantages of the present invention will become apparent from the following description.

DETAILED DESCRIPTION OF THE INVENTION AND PREFERRED EMBODIMENTS

Figure 1:
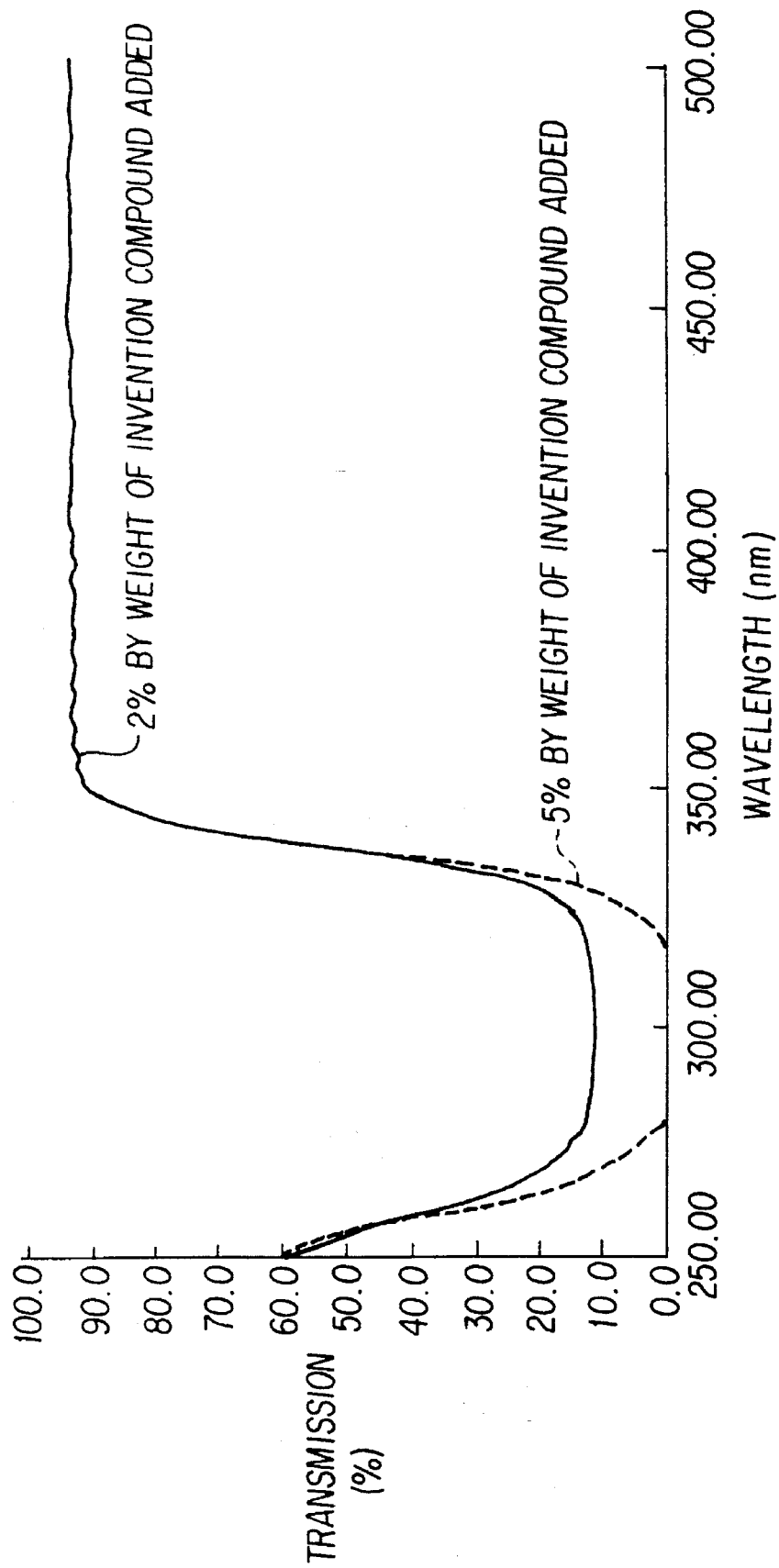
FIG. 1 is a graph showing the UV-B absorbing ability of the compound of the invention obtained in Test Example 2.

The phosphoric diesters of the present invention are represented by the formula (1) described above. In the formula, $R^1$ is an acyl group having at least one phenyl group. Due to the presence of this phenyl nucleus, the diesters of the present invention absorb UV rays having wavelengths between 290 to 320 nm. Among various acyl groups having at least one phenyl group, acyl groups having one to three phenyl or phenylene groups, such as a cinnamoyl group and a benzoyl group which may have a substituent are particularly preferred. Specific examples of the substituent include an alkoxy group, a hydroxy group, an amino group, an alkylamino group and a dialkylamino group. One to three of these substituents may be present on the phenyl group of the benzoyl group in any of the ortho, meta or para positions, preferably the ortho or para positions. Here, the alkoxy groups which are preferred are those having 1 to 22, in particular 1 to 10 carbon atoms. Specific examples of such preferable alkoxy groups include methoxy, ethoxy, propyloxy, isopropyloxy, n-butyloxy, tert-butyloxy, sec-butyloxy, isoamyloxy, n-hexyloxy, n-octyloxy, 2-ethylhexyloxy, dodecyloxy and hexadecyloxyo Preferable alkyl groups of the alkylamino group and the dialkylamino group are those having 1 to 22 carbon atoms, and more preferably, 1 to 10 carbon atoms. Specific examples of such alkyl groups include methyl, ethyl, propyl, isopropyl, n-butyl, tert-butyl, sec-butyl, isoamyl, n-hexyl, n-octyl, 2-ethylhexyl, dodecyl and hexadecyl. Examples of $R^1$ which are more preferred include p-methoxycinnamoyl, o-methoxycinnamoyl, p-ethoxycinnamoyl, o-ethoxycinnamoyl, o,p-dimethoxycinnamoyl, 3-hydroxy-4methoxycinnamoyi, benzoyl, p-(N,N-dimethylamino)benzoyl, p(N,N-diethylamino)benzoyl, p-hydroxybenzoyl, o-hydroxybenzoyl, p-aminobenzoyl and o-aminobenzoyl. Of these, p-methoxycinnamoyl is particularly preferred.

In the alkylene groups represented by $R^2$ in formula (1), preferable numbers of the oxygen atoms to be inserted are from 1 to 3. Specific examples of $R^2$ include ethylene, propylene, butylene, pentamethylene, hexamethylene, heptamethylene, octamethylene, nonamethylene, decamethylene, undecamethylene, dodecamethylene, 3-methylpentamethylene, monooxapentamethylene, trioxaundecamethylene, methylethylene, methylpropylene, methylbutylene and methylpentamethylene.

In formula (1), the alkyl group which may have an oxygen atom inserted therein and which is represented by L may be linear or branched, and preferably has 8 to 20 carbon atoms. Preferable numbers of the oxygen atoms to be inserted are from 1 to 3. Groups L having one inserted oxygen atom are alkoxyalkyl groups; groups L having two oxygen atoms are alkoxyalkoxy-alkyl groups, etc. Specific examples of L include ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, hexaeicosyl, 2-ethylhexyl, isostearyl, 3,7-dimethyloctyl, methoxyhexyl, ethoxyhexyl and 6-(2-ethylhexyloxy)hexyl.

Suitably, alkanolammonium and alkylammonium ions include mono-, di- and tri- alkanolammonium ions and mono-, di- and tri- alkylammonium ions. Specific examples of M include monovalent, divalent and trivalent ions such as hydrogen, sodium, potassium, barium, calcium, magnesium, aluminum, iron, ethanolammonium, ammonium and ethylammonium. Of these, calcium and aluminum are particularly preferred.

Compounds of formula (1) which are preferred are those in which $R^1$ is a cinnamoyl or benzoyl group which may be substituted, $R^2$ is a $C_{2\text{-}12}$ alkylene group, L is a $C_{8\text{-}20}$ linear or branched alkyl group or a group $R^1$-O-$R^2$- (wherein $R^1$ is a cinnamoyl group which may be substituted or a benzoyl group which may be substituted, and $R^1$ is a $C_{2\text{-}12}$ alkylene group), and M is a calcium atom or an aluminum atom. Among these compounds, those in which L is a $C_{2\text{-}20}$ linear or branched alkyl group are particularly preferred.

Specific examples of the particularly preferred compounds of formula (1) of the present invention include the compounds of following formulae (1a) to (1x):

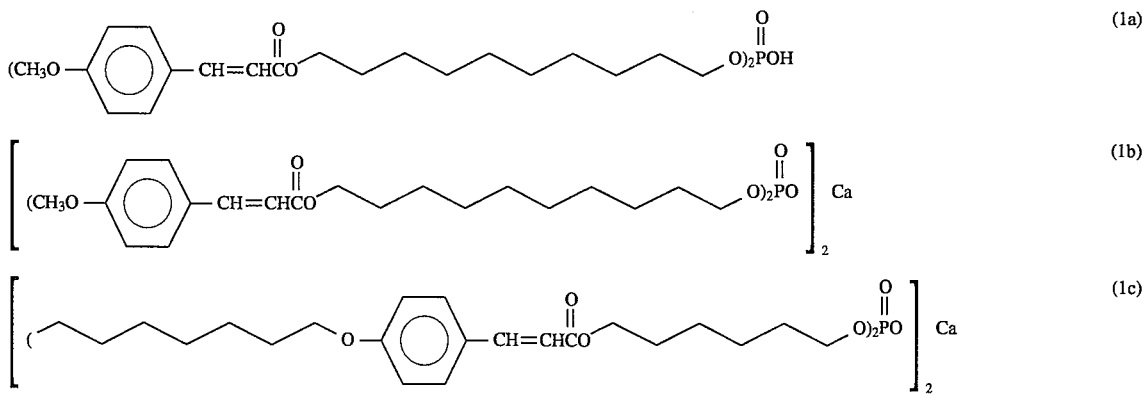

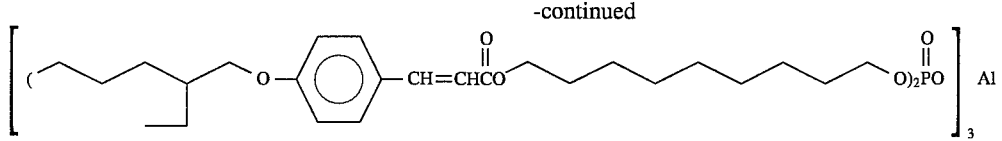
(1d)
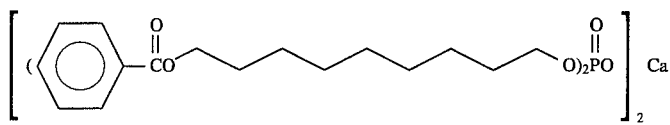
(1e)
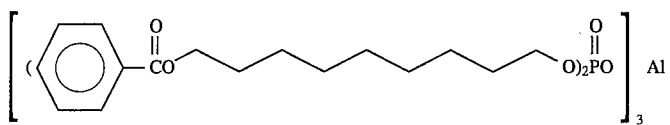
(1f)
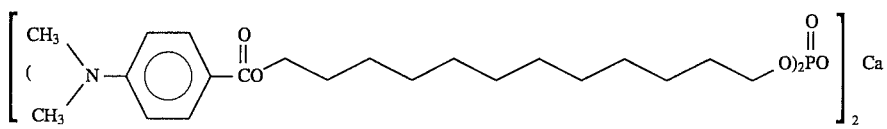
(1g)
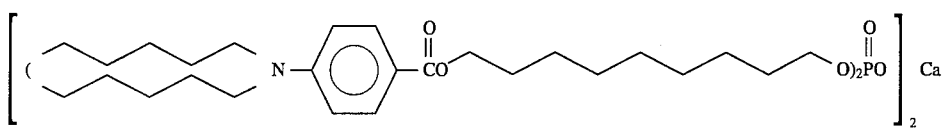
(1h)
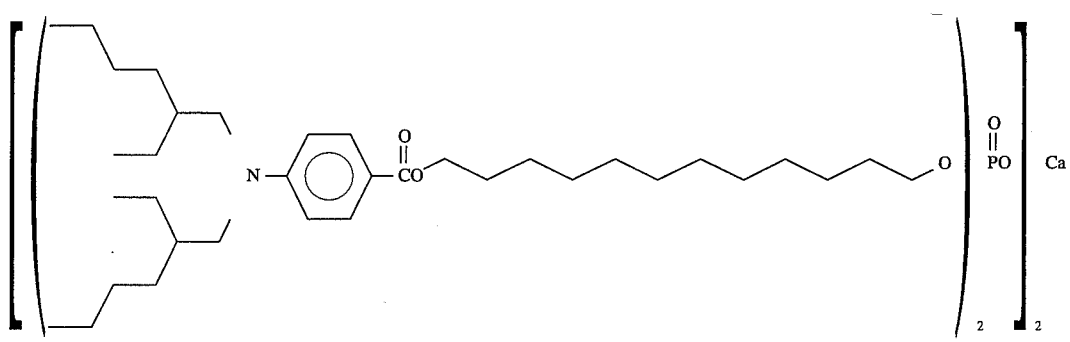
(1i)
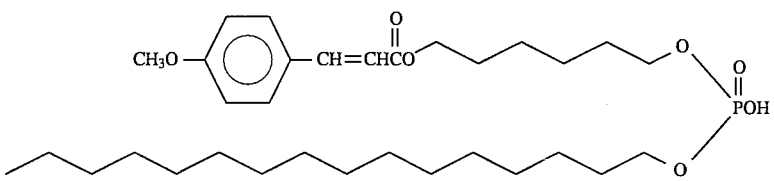
(1j)
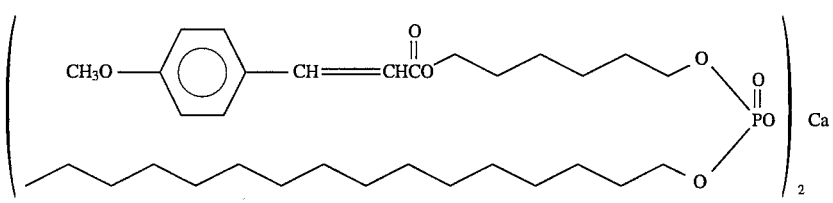
(1k)
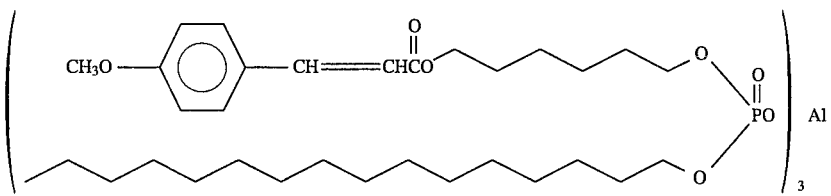
(1l)

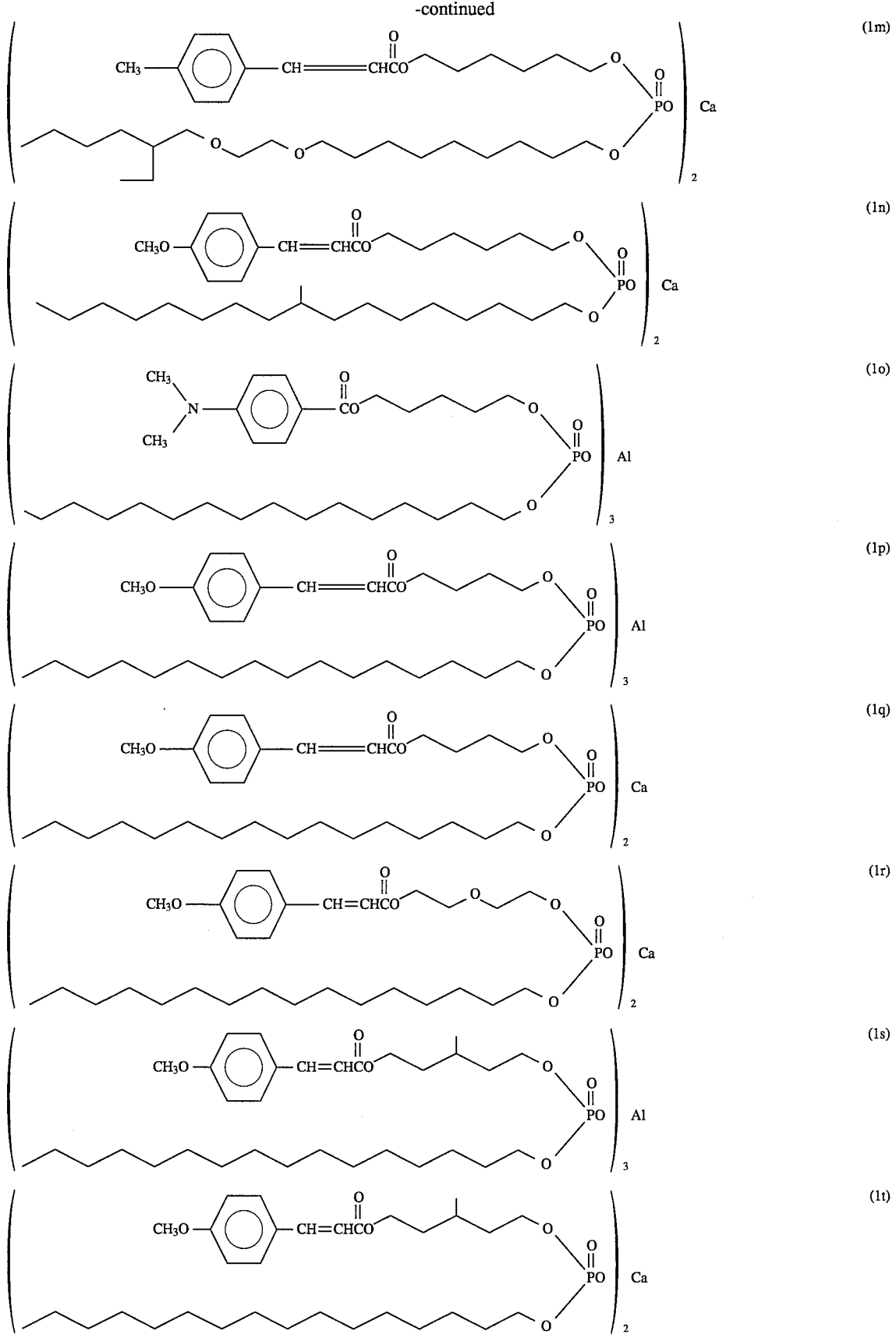

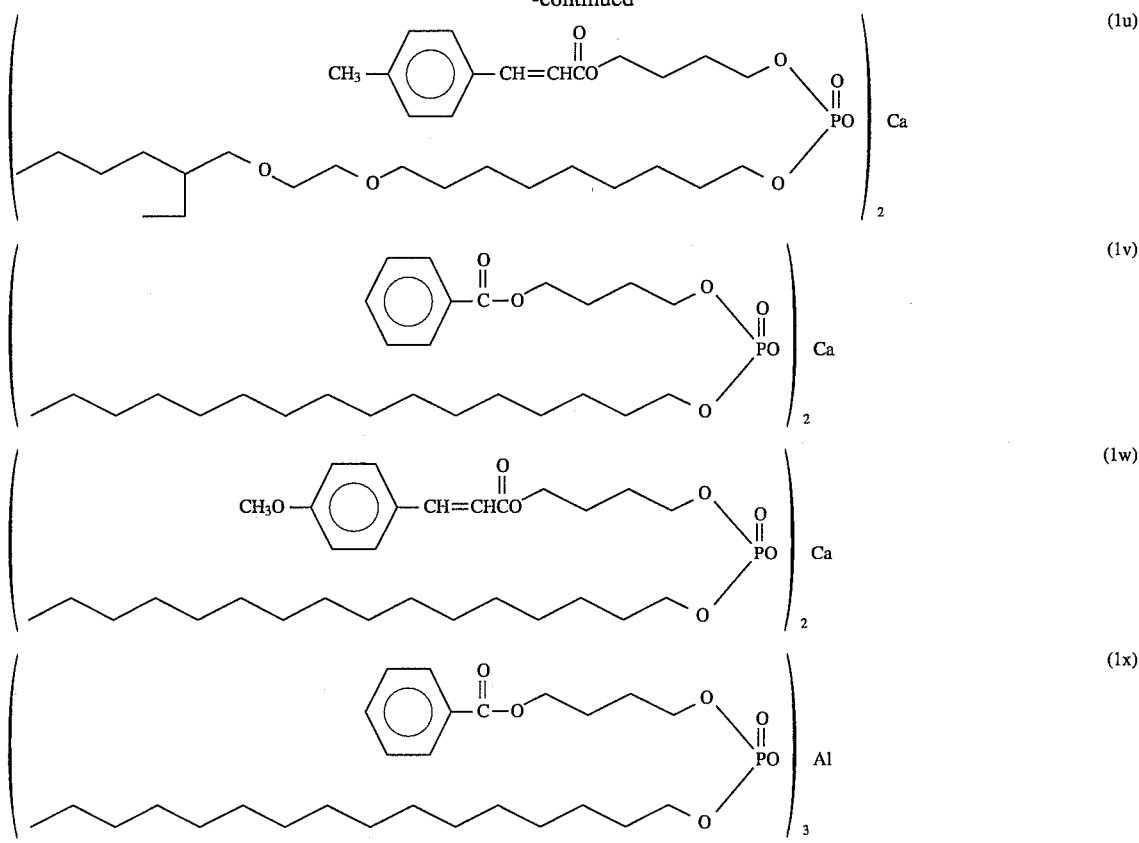

The compounds of formula (1) according to the present invention are prepared, for example, by the following reaction schemes A or B:

A. Preparation of Compounds (1a)—(1i) of Invention:

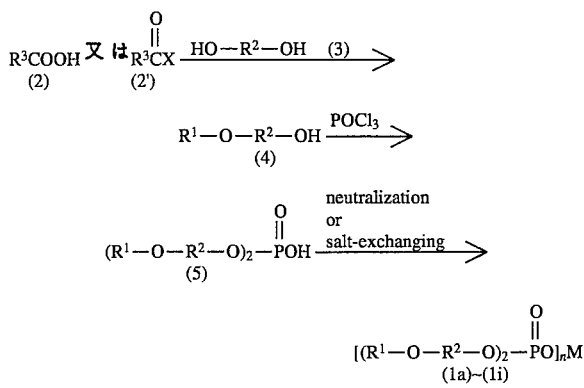

wherein $R^1$, $R^2$, n and M have the same meaning as defined herein before, $R^3$ is a residue of the acyl group represented by $R^1$ from which a carbonyl group is eliminated, and X represents a halogen atom.

In reaction scheme A, carboxylic acid (2) or an acid halide thereof (2') are reacted with diol (3) to obtain a monoester (4). The monoester (4) is reacted with phosphorus oxychloride to obtain a phosphoric diester (5), which is further converted into compounds (1b) to (1i) of the present invention by salt exchange or neutralization.

Reaction between carboxylic acid (2) and diol (3) is carried out in an inert solvent such as benzene, toluene or hexane, and in the presence of an acid catalyst such as para-toluenesulfonic acid, by using 1 to 10 fold, preferably 3 to 5 fold in moles, of diol (3) with respect to the amount of carboxylic acid (2) at 70° to 130° C. for 3 to 50 hours. The reaction between acid halide (2') and diol (3) may be carried out in the presence of a basic catalyst such as pyridine, a trialkylamine and an alkali metal hydroxide at 0° to 100° C. Reaction between the obtained monoester (4) and phosphorus oxychloride is carried out in an inert solvent such as tetrahydrofuran (THF), and in the presence of a base such as triethylamine, by using 1.5 to 2.5 fold, preferably 2.0 to 2.2 fold in moles, of monoester (4) with respect to the amount of the phosphorus oxychloride at −10° to 10° C. The thus obtained phosphoric diesters are neutralized or subjected to a salt-exchange process, i.e. are salified, using sodium hydroxide, potassium hydroxide, calcium chloride, calcium acetate, aluminum acetate and the like, in a polar solvent such as methanol, ethanol, water and the like to obtain the compounds (1a) to (1i) of the present invention with ease.

B. Preparation of Compounds (1j)–(1x) of Invention:

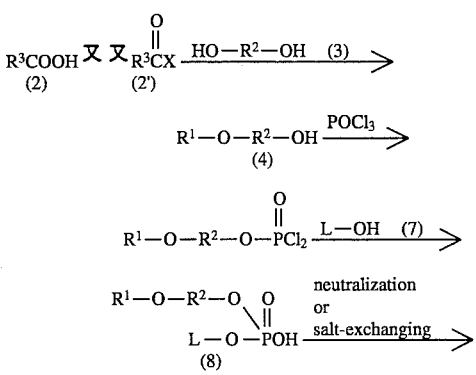

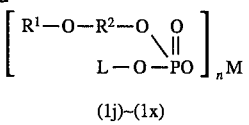

(1j)–(1x)

wherein $R^1$, $R^2$, $R^3$, L, n, M and X have the same meaning as defined herein before.

In reaction scheme B, carboxylic acid (2) or a halide thereof (2') are; reacted with diol (3) to obtain a monoester (4). The monoester (4) is reacted with phosphorus oxychloride at a low temperature to obtain an intermediate (6), which is further reacted with alcohol (7) to obtain a phosphoric diester (8). Compounds (1k) to (1x) of the present invention are obtained by salt exchanging of the diester (8).

The reaction for producing intermediate (6) from monoester (4) and phosphorus oxychloride is carried out in an inert solvent such as THF, and in the presence of a base such as triethylamine, by using 0.5 to 1.5 fold, preferably 1.0 to 1.1 fold in moles, of monoester (4) with respect to the amount of phosphorus oxychloride at $-80°$ to $10°$ C., preferably at $-50°$ to $5°$ C. The reaction between the intermediate (6) and alcohol (7) may be carried out in the presence of an inert solvent such as THF, using 1.0 to 1.5 fold, preferably 1.0 to 1.1 fold in moles, of alcohol (7) with respect to the intermediate (6). The thus obtained phosphoric diesters (8) are neutralized or subjected to a salt-exchange process using sodium hydroxide, potassium hydroxide, calcium chloride, calcium acetate, aluminum acetate and the like, in a polar solvent such as methanol, ethanol, water and the like, to obtain the compounds (1h) to (1w) of the present invention with ease.

The compounds (1) of the present invention obtained as described above exhibit excellent UV absorbing effects, in particular, excellent UV-B absorbing effect. In addition, they are excellent in forming a gel of various oils and organic oil-based UV absorbers, and accordingly, are useful for preparing cosmetic compositions having long-lasting effects, in other words, compositions which remain on the skin while holding the organic oil-based UV absorbers.

The "various oils" mentioned above are hydrocarbon oils, ester oils, silicone oils, and animal and vegetable oils, which are usually employed for inhibiting evaporation of moisture from the skin or improving organoleptic sensation. Preferred oils are aromatic hydrocarbon oils, aliphatic hydrocarbon oils, saturated or unsaturated oils and fats, and synthetic ester oils which readily form a thixotropic gel with phosphoric diester salts of the present invention. Specific examples of the oils include liquid paraffin, squalane, hexadecane, isohexadecane, dicapric neopentyl glycol, diisopropyl adipate, myristyl isooctanoate, 1-isostearoyl-3-myristoyl glycerin, hexyl laurate, jojoba oil, octyldodecyl oleate, oleyl oleate and glyceryl trioctanoate, Examples of the organic oil-based UV absorbers include benzophenone derivatives, p-aminobenzoic acid derivatives p-methoxycinnamic acid derivatives and salicylic acid derivatives. More specifically, 2-ethylhexyl para-methoxycinnamate, 2-ethylhexyl para-N,N-dimethylaminobenzoate, 2-ethylhexyl para-aminobenzoate and 2-ethylhexyl para-methoxylsalicylate are mentioned.

No particular limitation is imposed on the amount of the compounds (1) of the present invention to be incorporated with a cosmetic base to form the cosmetic compositions of the invention. However, it should be borne in mind that when the amounts are too small, the UV absorbing effect of the cosmetic compositions becomes poor, and when the amounts are excessive, feel sensed by the skin deteriorates.

Accordingly, it is preferred that the amounts be in the range from 0.01 to 80% and more particularly from 0.1 to 30% by weight. With regard to the various oils mentioned above, the amounts are in the range from 0.1 to 99.9% and more particularly from 1.0 to 80% by weight.

The cosmetic compositions of the present invention may also contain optional ingredients other than the essential ingredients described above as long as the effects of the invention are not impeded. Such optional ingredients include solid or semi-solid oils or fats, humectants, intercellular lipids (ceramides, etc), other UV absorbers than described above, chelating agents, pH modifiers, preservatives, thickeners, colorants, perfumes, pharmaceuticals, emulsifiers such as anionic surfactants and nonionic surfactants (including polyether-modified silicones), detergents, inorganic pigments and organic powder materials.

The cosmetic compositions according to the present invention are prepared by mixing and stirring the above-mentioned ingredients in a conventional manner. Because the compounds (1) of the present invention are capable of gelling the above-mentioned various oils and organic oil-based UV absorbers as described above, they are useful for preparing cosmetic compositions of both an O/W (oil-in-water) emulsion type or a W/O (water-in-oil) emulsion type. In more concrete terms, emulsions, creams, foundations and the like can be prepared.

The cosmetic compositions of the present invention which contain compound (1) of the present invention do not readily permeate into the skin or evaporate from the surface of the skin. Therefore, they exhibit excellent UV shielding effects over a prolonged period and are very safe to the skin.

EXAMPLES

The present invention will now be described in detail by way of examples, which are not intended to limiting the invention.

In the following Examples and Test Examples, compounds (1a) to (1w) are identical to those, referred to hereinbefore.

Example 1

Synthesis of Compound (1a)

1) 20 g (0.112 mol) of p-methoxycinnamic acid, 90 g (0.517 mol) of 1,10-decanediol, 0.5 g of p-toluenesulfonic acid, 300 ml of toluene and 150 ml of hexane were placed in a 1-liter four-necked flask equipped with a Deanstark trap, and refluxed, while introducing nitrogen gas, until no water came out. After completion of the reaction, the mixture was washed with saturated sodium bicarbonate solution and dried over anhydrous magnesium sulfate, followed by filtration and evaporation of solvent. Purification by silica gel chromatography yielded 38 g of a monoester as white crystals. The purity was found to be 98% by gas chromatography (GLC) analysis. 200 MHz $^1$H-NMR (solvent: $CDCl_3$, TMS standard) confirmed proton signals of hydroxy at $\delta=1.7$, methoxy at $\delta=3.8$, methylene at $\delta=1.5–1.9$, 3.7 and 4.2, olefin at $\delta=6.3$ and 7.7, and an aromatic ring at $\delta=6.9$ and 7.5.

2) 0.93 g (6.078 mmol) of phosphorus oxychloride was dissolved in THF, and the solution was placed in a 100 ml four-necked flask. The flask was ice-cooled while nitrogen gas was introduced. 30 ml of THF containing 4.43 g (13.3 mmol) of the monoester obtained in the step 1) above and 1.22 g of triethylamine as dissolved was added dropwise into the flask. The reaction temperature was maintained between −5° to 5° C., and under this condition, stirring was continued for 24 hours. Thereafter, 0.25 g of water and 0.62 g of triethylamine were added and stirring was started again. The stirring continued at 0° C. for 24 hours. The resulting pellet was removed by filtration, and solvent was distilled off. The residue was dissolved in ethyl acetate and washed. The residue obtained from distilling the solvent was dispersed in 50 ml of 1N hydrochloric acid and stirred at 50° C. for 7 hours, followed by cooling to room temperature. Extraction was performed using ethyl acetate. As a result, 2.5 g of phosphoric diester (1a) was obtained as white crystals. 200 MHz $^1$H-NMR (solvent: $CDCl_3$, TMS standard) confirmed proton signals of methoxy at δ=3.8, methylene at δ=1.3–1.7, 3.95–4.15 and 4.2, olefin at δ=6.3 and 7.7, and an aromatic ring at δ=6.9 and 7.5. $^{31}$P-NMR revealed a purity of 99%.

Example 2

Synthesis of Compound (1b)

1.4 g of the phosphoric diester (1a) obtained in Example 1 was dissolved in ethanol. To the solution, 1.0 g of calcium acetate, water and ethanol were added and mixed at 60° C. for 5 hours with stirring. Subsequently, twice the amount of water was added thereto and allowed to cool to room temperature. The resulting pellet was collected by filtration, washed with water and acetone, and dried. As a result, 1.3 g of a calcium salt (1b) of phosphoric diester was obtained as a white solid. 200 MHz $^1$H-NMR (solvent: $CDCl_3$ TMS standard) confirmed proton signals of methoxy at δ=3.8, methylene at δ=1.2–1.6, 3.75–3.95 and 4.2, olefin at δ=6.3 and 7.7, and an aromatic ring at δ=6.9 and 7.5. $^{31}$P-NMR revealed a purity of 99%.

Example 3

Synthesis of Compound (1j)

1) 70 g (0.393 mol) of p-methoxycinnamic acid, 266 g (2.25 mol) of 1,6-hexanediol, 2.0 g of p-toluenesulfonic acid, 600 ml of toluene and 300 ml of hexane were placed in a 2-liter four-necked flask equipped with a Deanstark trap, and refluxed, while introducing nitrogen gas, until no water came out. After completion of the reaction, the mixture was washed with saturated sodium bicarbonate solution and dried over anhydrous magnesium sulfate, followed by filtration and evaporation of solvent. As a result, 92.6 g of a monoester was obtained as white crystals. The purity was found to be 95% by GLC analysis. 200 MHz $^1$H-NMR (solvent: $CDCl_3$, TMS standard) confirmed proton signals of hydroxy at δ=1.7, methoxy at δ=3.8, methylene at δ=1.5–1.9, 3.7 and 4.2, olefin at δ=6.3 and 7.7, and an aromatic ring at δ=6.9 and 7.5.

2) 15.8 g (0.103 mol) of phosphorus oxychloride was dissolved in THF, and the solution was placed in a 300 ml four-necked flask. The flask was cooled to −60° C. while nitrogen gas was introduced. 100 ml of THF containing 30 g (0.108 mol) of the monoester synthesized in the step 1) above and 11 g of triethylamine as dissolved was added dropwise into the flask with stirring. The reaction temperature was maintained not higher than −30° C., and under this condition, stirring was continued for 3 hours. Thereafter, the temperature was raised to 0° C., and a THF solution containing 26.1 g (0.108 mol) of hexadecanol and 11 g of triethylamine was added dropwise thereto. During the addition, the temperature was controlled to be not higher than 5° C. The mixture was stirred at 0° C. for 24 hours, then 2 g of water was added thereto. Stirring was continued for further 6 hours. Subsequently, the resulting pellet was removed by filtration, and solvent was distilled off. The residue was dissolved in ethyl acetate and washed with diluted hydrochloric acid and water in this order. The solid obtained after the solvent distilled off was washed with ether. As a result, 30 g of phosphoric diester (1j) obtained as white crystals. 200 MHz $^1$H-NMR (solvent: $CDCl_3$, TMS standard) confirmed proton signals of methoxy at δ=3.8, methyl at δ=0.8–0.9, methylene at δ=1.2–1.6, 3.95–4.15 and 4.2, olefin at δ=6.3 and 7.7, and an aromatic ring at δ=6.9 and 7.5. $^{31}$P-NMR revealed a purity of 99%.

Example 4

Synthesis of Compound (1k)

14 g of the phosphoric diester (1j) obtained in Example 3, step 2) was dissolved in ethanol. To the solution, 10 g of calcium acetate, water and ethanol were added and mixed at 60° C. for 5 hours. Subsequently, twice the amount of water was added thereto and allowed to cool to room temperature. The pellet was collected by filtration, washed with water and acetone, and dried. As a result, 14 g of a calcium salt (1k) of the phosphoric diester was obtained as a white solid. 200 MHz $^1$H-NMR (solvent: $CDCl_3$, TMS standard) confirmed proton signals of methoxy at δ=3.8, methyl at δ=0.8–0.9, methylene at δ=1.2–1,.6, 3.75–3.95 and 4.2, olefin at δ=6.3 and 7.7, and an aromatic: ring at δ=6.9 and 7.5. $^{31}$P-NMR revealed a purity of 99%.

Example 5

Synthesis of Compound (1l)

10 g of the phosphoric diester (1j) obtained in Example 3, 2) was dissolved in ethanol. To the solution, 10 g of aluminum acetate, water and ethanol were added and mixed at 50° C. for 1 hour. Subsequently, twice the amount of water was added thereto and allowed to cool down to room temperature. The pellet was collected by filtration, washed with water and acetone, and dried. As a result, 10 g of an aluminum salt (1l) of the phosphoric diester was obtained as a white solid. 200 MHz $^1$H-NMR (solvent: $CDCl_3$ TMS standard) confirmed proton signals of methoxy at δ=3.8, methyl at δ=0.8–0.9, methylene at δ=1.2–1.6, 3.9–4.1 and 4.2, olefin at δ=6.3 and 7.7, and an aromatic ring at δ=6.9 and 7.5. $^{31}$P-NMR revealed a purity of 99%.

Example 6

Synthesis of Compound (1c)

1) 25 g (0.152 mol) of p-hydroxycinnamic acid was dissolved in 100 ml of methanol, to which 1 g of concentrated sulfuric acid was added and refluxed for 8 hours. After allowing the system to cool down to room temperature, twice the amount of water was added thereto. The pellet was collected by filtration, washed with water, and dried. 25 g of a yellowish white solid was obtained. The solid was recrystallized from toluene. As a result, 21 g of methyl para-hydroxycinnamate was obtained as a yellowish white solid.

2) 10 g (0.056 mol) of methyl p-hydroxycinnamate obtained in the step 1) above was dissolved in 50 ml of acetone; to which 7.8 g (0.057 mol) of potassium carbonate was added. To the obtained mixture, 12 g (0.062 mol) of 1-octylbromide was added, and refluxed with heating for 50 hours. After allowing the system to cool to room temperature, the obtained pellet was removed by filtration. Solvent was distilled off from the mother liquid of filtration, and the residue was dissolved in 100 ml of ethyl acetate, and washed with water. Solvent was further distilled off to obtain 15 g of yellowish white crystals. The crystals were recrystallized from hexane, and as a result, 14 g of methyl para-octyloxycinnamate was obtained as a white solid.

3) 8.0 g (0.028 mol) of methyl p-octyloxycinnamate obtained in the step 2) above, 40 g (0.198 mol) of 1,6-hexanediol and 0.35 g of p-toluenesulfonic acid were added to 100 ml of toluene, and refluxed for 20 hours with heating using a Deanstark trap. After cooled to room temperature, the contents were diluted with 300 ml of toluene, water, saturated sodium bicarbonate solution and saturated sodium chloride solution in this order, then dried with anhydrous sodium sulfate, followed by filtration and evaporation of solvent. The obtained residue was purified by silica gel column chromatography to obtain 9.2 g of hexanediol monopara-octyloxycinnamate as a yellow oil. The purity was found to be 98% by GLC analysis. 200 MHz $^1$H-NMR (solvent: CDCl$_3$, TMS standard) confirmed proton signals of methyl at δ=0.9, methylene at δ=1.4–1.9, 3.7, 4.0 and 4.2, hydroxy at δ=1.6, olefin at δ=6.3 and 7.7, and an aromatic ring at δ=6.9 and 7.5.

4) 0.956 g (0.006 mmol) of phosphorus oxychloride was dissolved in THF and placed in a 100 ml four-necked flask. The flask was ice-cooled while nitrogen was introduced. 5.0 g (0.013 mol) of the monoester obtained in the step 3) above and 1.31 g of triethylamine were dissolved in 50 ml of THF, and the solution was added to the flask dropwise. The reaction temperature was maintained at –5° to 5° C. Stirring was continued for further 24 hours, then 1 g of water was added. Stirring was started again for 24 hours at 0° C. Subsequently, the pellet was removed off by filtration, and solvent was distilled off. The residue was dispersed in 100 ml of 2N HCl, stirred for 4 hours at 40° C. After the dispersion was allowed to cool down to room temperature, it was subjected to extraction using ethyl acetate and then washed. Solvent was distilled off, and the obtained residue was dissolved in ethanol. To the ethanol solution, 5.0 g of calcium acetate and water were added and stirred at 40° C. for 1 hour. Twice the amount of water was added thereto and cooled to room temperature. The pellet was collected by filtration and washed with water and acetone, followed by drying. As a result, 3.6 g of phosphoric diester calcium salt (1c) was obtained as a white solid. 200 MHz $^1$H-NMR (solvent: CDCl$_3$, TMS standard) confirmed proton signals of methyl at δ=0.9, methylene at δ=1.3–1.75, 3.7, 3.9 and 4.2, olefin at δ=6.3 and 7.7, and an aromatic ring at δ=6.9 and 7.5. $^{31}$P-NMR revealed a purity of 98%.

Example 7

Synthesis of Compound (1p)

1) 100 g (0.562 mol) of p-methoxycinnamic acid, 250 g (2.78 mol) of 1,4-butanediol, 4.0 g of p-toluenesulfonic acid and 300 ml of toluene were placed in a 2-liter four-necked flask equipped with a Deanstark trap, and refluxed, while introducing nitrogen gas, until no water came out. After completion of the reaction, the contents were diluted with twice the amount of toluene, then washed with water, saturated sodium bicarbonate solution, water and saturated sodium chloride solution in this order. The washed material was dried with anhydrous magnesium sulfate, followed by filtration and evaporation of solvent. 134.5 g of a monoester was obtained as white crystals. The purity was found to be 95% by GLC analysis. 200 MHz $^1$H-NMR (solvent: CDCl$_3$, TMS standard) confirmed proton signals of hydroxy at δ=1.7, methoxy at δ=3.8, methylene at δ=1.55, 1.6–1.9, 3.7 and 4.25, olefin at δ=6.3 and 7.7, and an aromatic ring at δ=6.9 and 7.5.

2) 17 g (0.11 mol) of phosphorus oxychloride was dissolved in THF, and the solution was placed in a 500 ml four-necked flask. The flask was cooled to –60° C. while nitrogen gas was introduced. 100 ml of THF containing 31 g (0.118 mol) of the monoester synthesized in the step 1) above and 11.5 g of triethylamine as dissolved was added dropwise into the flask. The reaction temperature was maintained not higher than –30° C., and under this condition, stirring was continued for 3 hours. Thereafter, the temperature was raised to 0° C., and a THF solution containing 30 g (0.124 mol) of hexadecanol and 11.5 g of triethylamine was added thereto dropwise. During the addition, the reaction temperature was maintained not higher than 5° C. Stirring was performed for 24 hours at 0° C. and then 2 g of water was added. Stirring was continued for further 6 hours. The pellet was removed off by filtration, and solvent was distilled off. The residue was dissolved in ethyl acetate and washed with diluted HCl and water in this order. Solvent was distilled off and the residue was recrystallized from hexane to obtain 50 g of phosphoric diester as white crystals. 200 MHz $^1$H-NMR (solvent: CDCl$_3$, TMS standard) confirmed proton signals of methoxy at δ=3.8, methyl at δ=0.8–0.9, methylene at δ=1.2–1.5, 1.7, 1.85 and 3.85, 4.1 and 4.25, olefin at δ=6.3 and 7.7, and an aromatic ring at δ=6.9 and 7.5. $^{31}$P-NMR revealed a purity of 99%.

3) 15 g of the phosphoric diester obtained in step 2) above was dissolved in ethanol. To the solution, 10 g of aluminum acetate, water and ethanol were added and mixed at 60° C. for 5 hours. Subsequently, twice the amount of water was added thereto and allowed to cool down to room temperature. The pellet was collected by filtration, washed with water and acetone, and dried. As a result, 15 g of an aluminum salt (1p) of phospholic diester was obtained as a white solid. 200 MHz $^1$H-NMR (solvent: CDCl$_3$ TMS standard) confirmed proton signals: of methoxy at δ=3.8, methyl at δ=0.8–0.9, methylene at δ=1.2–1.5, 1.6, 1.75 and 3.85, 3.95 and 4.25, olefin at δ=6.3 and 7.7, and an aromatic ring at δ=6.9 and 7.5. $^{31}$P-NMR revealed a purity of 99%.

Example 8

Synthesis of Compound (1w)

15 g of the phosphoric diester (1p) obtained in Example 7, 2) was dissolved in ethanol. To the solution, 10 g of calcium acetate, water and ethanol were added and mixed at 60° C. for 5 hours with stirring. Subsequently, twice the amount of water was added thereto and allowed to cool down to room temperature. The pellet was collected by filtration, washed with water and acetone, and dried. As a result, 15 g of a calcium salt (1w) of phosphoric diester was obtained as a white solid. 200 MHz $^1$H-NMR (solvent: CDCl$_3$, TMS standard) confirmed proton signals of methoxy at δ=3.8, methyl at δ=0.8–0.9, methylene at δ=1.2–1.6, 1.75 and 3.85, 3.95 and 4.2, olefin at δ=6.3 and 7.7, and an aromatic ring at δ=6.9 and 7.5. $^{31}$P-NMR revealed a purity of 99%.

Example 9

Synthesis of Compound (1t)

1) 41 g (0.23 mol) of p-methoxycinnamic acid, 266 g (2.25 mol) of 3-methylpentanediol, 1.0 g of p-toluenesulfonic acid and 600 ml of toluene were placed in a 2-liter four-necked flask equipped with a Deanstark trap, and refluxed, while introducing nitrogen gas, until no water came out. After completion of the reaction, the contents were washed with saturated sodium bicarbonate solution, then dried with anhydrous magnesium sulfate, followed by filtration and evaporation of solvent. 53 g of a monoester was obtained as a colorless viscous liquid. The purity was found to be 95% by GLC analysis. 200 MHz $^1$H-NMR (solvent: CDCl$_3$, TMS standard) confirmed proton signals of hydroxy at δ=1.7, methoxy at δ=3.8, methyl at δ=1.0, methylene at δ=1.5–1.9, 3.7 and 4.2, olefin at δ=6.3 and 7.7, and an aromatic ring at δ=6.9 and 7.5.

2) 15.3 g (0.100 mol) of phosphorus oxychloride was dissolved in THF, and the solution was placed in a 300 ml four-necked flask. The flask was cooled to −60° C. while nitrogen gas was introduced. 100 ml of THF containing 30 g (0.108 mol) of the monoester synthesized in the step 1) above and 11 g of triethylamine as dissolved was added dropwise with stirring into the flask. The reaction temperature was maintained not higher than −30° C., and under this condition, stirring was continued for 3 hours. Thereafter, the temperature was raised to 0° C., and a THF solution containing 26.1 g (0.108 mol) of hexadecanol and 11 g of triethylamine was added thereto dropwise. During the addition, the reaction temperature was maintained not higher than 5° C. Stirring was performed for 24 hours at 0° C., and then, 2 g of water was added. Stirring was continued for a further 6 hours. The pellet was removed by filtration, and solvent was distilled off. The residue was dissolved in ethyl acetate and washed with diluted HCl and water in this order. Solvent was distilled off and the residue was washed with ether to obtain 30 g of phosphoric diester as white crystals. 200 MHz $^1$H-NMR (solvent: CDCl$_3$, TMS standard) confirmed proton signals of methoxy at δ=3.8, methyl at δ=0.8–0.9 and 1.0, methylene at δ=1.2–1.,6, and 3.95–4.15 and 4.2, olefin at δ=6.3 and 7.7, and an aromatic ring at δ=6.9 and 7.5. $^{31}$p-NMR revealed a purity of 99%.

3) 14 g of the phosphoric diester obtained in step 2) above was dissolved in ethanol. To the solution, 10 g of calcium acetate, water and ethanol were added and mixed at 60° C. for 5 hours. Subsequently, twice the amount of water was added thereto and allowed to cool to room temperature. The pellet was collected by filtration, washed with water and acetone, and dried. As a result, 14 g of a calcium salt (1t) of the phosphoric diester was obtained as a white solid. 200 MHz $^1$H-NMR (solvent: CDCl$_3$, TMS standard) confirmed proton signals of methoxy at δ=3.8, methyl at δ=0.8–0.9 and 1.0, methylene at δ=1.2–1.6 and 3.8–4.0 and 4.2, olefin at δ=6.3 and 7.7, and an aromatic ring at δ=6.9 and 7.5. $^{31}$P-NMR revealed a purity of 99%.

Example 10

Synthesis of Compound (1v)

1) 64 g (0.525 mol) of benzoic acid, 500 g (5.68 mol) of 1,4-butanediol, 0.5 g of p-toluenesulfonic acid and 500 ml of toluene were placed in a 2-liter four-necked flask equipped with a Deanstark trap, and refluxed until no water came out. After completion of the reaction, the contents were diluted with twice the amount of toluene, then washed with saturated sodium bicarbonate solution, water and saturated sodium chloride solution in this order. The washed material was dried with anhydrous magnesium sulfate, followed by filtration and evaporation of solvent. 80 g of a monoester was obtained as a colorless oil. 200 MHz $^1$H-NMR (solvent: CDCl$_3$, TMS standard) confirmed proton signals of methylene at δ=1.55–2.0, 3.68 and 4.35, aromatic ring at δ=8.05 and 7.4–7.6 and hydroxy at δ=2.65.

2) 25 g (0.163 mol) of phosphorus oxychloride was dissolved in THF, and the solution was placed in a 500 ml four-necked flask. The flask was cooled to a temperature not higher than −50° C. with dry ice/acetone while nitrogen gas was introduced. About 50 ml of THF containing 32.3 g (0.167 mol) of monobenzoate (4-benzoyloxy-1-butanol) and 16.5 g (0.163 mol) of triethylamine as dissolved was added dropwise into the flask. The reaction temperature was maintained not higher than −30° C., and under this condition, stirring was continued for 3 hours Thereafter, the temperature was raised to 0° C. and about 100 ml of a THF solution containing 41.5 g (0.171 mol) of 1-hexadecanol and 16.5 g (0.163 mol) of triethylamine was added thereto dropwise. During the addition, the reaction temperature was maintained not higher than 5° C. Stirring was performed overnight with ice-cooling, and then, 10 g of water was added. Stirring was continued for a while. The white pellet obtained (hydrochloride) was removed by filtration, and the solvent was distilled off. The residue was dissolved in about 200 ml of 2N HCl, and stirred for 2 hours at 40°–50° C. After the mixture was allowed to cool, twice the amount of water was added for dilution. The pellet was collected by filtration, and washed with water. Recrystallization from ethanol yielded 50 g of phosphoric diester as white crystals. 200 MHz $^1$H-NMR (solvent: CDCl$_3$, TMS standard) confirmed proton signals of methyl at δ=0.80.9, methylene at δ=1.2–1.6, 3.9–4.1 and 4.35 olefin at δ=6.3 and 7.7, and an aromatic ring at δ=8.05 and 7.4–7.6. $^{31}$P-NMR revealed a purity of 99%.

3) 20 g of the phosphoric diester obtained in step 2) above was dissolved in 100 ml of ethanol. To the solution, 19 g of calcium acetate dissolved in water was added and stirred at 50° C. for 2 hours. Subsequently, twice the amount of water was added thereto and allowed to cool down to 0° C. The pellet was collected by filtration, washed with water and acetone, and dried. As a result, 20 g of a calcium salt (1v) of phosphoric diester was obtained as a white solid. 200 MHz $^1$H-NMR (solvent: CDCl$_3$, TMS standard) confirmed proton signals of methyl at δ=0.8–0.9, methylene at δ=1.2–1.6 and 3.7–3.9 and 4.35, and an aromatic ring at δ=8.05 and 7.4–7.6. $^{31}$P-NMR revealed a purity of 99%.

Test Example 1

Gel-forming ability on oils

Various metal salts of phosphoric diesters were evaluated with regard to gel-forming ability on oils. In the test, 1 g of each compound was put in a test tube, and 19 g of an oil agent was added thereto. The content was mixed with an ultrasonic mixer for about 3 minutes to obtain a uniform dispersion or solution. The resulted dispersion or solution was allowed to stand overnight, then the state of the liquid was visually observed and evaluated based on the following criteria:

A: Transparent and viscous gel formed

B: Gel of low viscosity formed

C: Gel formed but oil oozed

X: Solution/Uniform dispersion was not formed.

The results are shown in Table 2.

|  | Present Invention | | | | | | | Comp. |
| --- | --- | --- | --- | --- | --- | --- | --- | --- |
| Oils | (1b) | (1c) | (1k) | (1p) | (1l) | (1t) | (1v) | Ex.[1] |
| Toluene | A | A | A | A | A | A | A | X |
| Diisopropyl adipate | C | C | C | A | B[2] | B[2] | A | X |
| Neopentylglycol dicaprate | C | C | C | A | C | C | A | X |
| 2-Ethylhexyl paramethoxy-cinnamate | A | A | A | A | A | A | B | X |

[1] 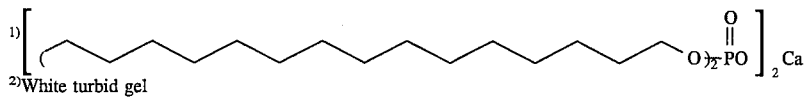

[2] White turbid gel

From the results in Table 2, it is apparent that the compounds of the present invention are effective in forming gels of hydrophilic oils having an aromatic ring or an ester bond.

Test Example 2

UV absorbing ability

An oil gel was prepared by adding compound (1l) of the present invention to an oil agent (diisopropyl adipate). 10 mg of the gel was sandwiched by quartz plates (length of light path: 8 micrometers), and the UV spectrum was obtained (FIG. 1). As the FIG. 1 shows, excellent UV-B absorbing ability was confirmed.

Example 11

An anti-suntan cream of the O/W type having the following formulation was prepared according to a conventional method.

| Formulation: | |
| --- | --- |
| Compound (1b) of Example 2 | 3.0 (wt) |
| Monocetyl phosphate | 0.5 |
| Squalane | 2.0 |
| Isopropyl palmitate | 2.0 |
| Olive oil | 2.0 |
| Dimethylpolysiloxane | 2.0 |
| Butyl paraben | 0.1 |
| Glycerol | 5.0 |
| L-Arginine | 0.5 |
| Ethanol | 5.0 |
| Methyl paraben | 0.3 |
| Carbopol 941 (product of BF Goodrich) | 0.25 |
| Purified water | Balance |

This cream provided excellent safety for the skin, and the UV shielding effect of the cream lasted a long time.

Example 12

An anti-suntan foundation of the W/O type having the following formulation was prepared according to a conventional method.

| Formulation: | |
| --- | --- |
| Compound (1l) of Example 5 | 10.0 (wt %) |
| Squalane | 10.0 |
| Dimethylpolysiloxane | 5.0 |
| Perfluoropolyether | 15.0 |
| Dimethylpolysiloxane-polyoxyalkylene copolymer | 2.0 |
| Glycerol | 2.0 |
| Purified water | Balance |

-continued

| Formulation: | |
| --- | --- |
| Pigment: | |
| Sericite | 6.0 |
| Titanium oxide | 8.0 |
| Iron oxide (red, yellow, black) | 1.2 |
| Nylon powder | 5.0 |
| Perfume | 0.06 |

This foundation provided excellent safety for the skin, and the UV shielding effect of the foundation lasted a long time.

Example 13

A dual-phase anti-suntan emulsion having the following formulation was prepared according to a conventional method.

| Formulation: | |
| --- | --- |
| Compound (1k) of Example 4 | 5.0 (wt) |
| Liquid paraffin | 10.0 |
| Squalane | 5.0 |
| Octamethyl cyclotetrasiloxane | 5.0 |
| Perfluoropolyether | 10.0 |
| Dimethylpolysiloxane-polyoxyalkylene copolymer | 1.0 |
| Glycerol | 2.0 |
| Ethanol | 5.0 |
| Zinc oxide | 7.5 |
| Octyl methoxycinnamate | 2.0 |
| Perfume | 0.01 |
| Purified water | Balance |

This emulsion provided excellent safety for the skin, and the UV shielding effect of the emulsion lasted a long time.

Example 14

An anti-suntan cream of the O/W type having the following formulation was prepared according to a conventional method.

| Formulation: | |
| --- | --- |
| Compound (1t) of Example 9 | 0.5 (wt %) |
| Neopentylglycol dicaprate | 5.0 |
| Jojoba oil | 1.0 |
| Methylphenyl polysiloxane | 3.0 |
| Cetanol | 2.0 |
| Stearyl alcohol | 1.0 |
| Self-emulsified glycerin monostearate | 2.0 |
| Sorbitan monostearate | 1.0 |

-continued

| Formulation: | |
|---|---|
| 2-Ethylhexyl p-methoxycinnamate | 5.0 |
| Butyl paraben | 0.2 |
| Glycerol | 5.0 |
| Ethanol | 1.0 |
| Methyl paraben | 0.5 |
| Purified water | Balance |

This cream provided excellent safety for the skin, and the UV =shielding effect of the cream lasted a long time.

Example 15

An anti-suntan cream of the W/O type having the following formulation was prepared according to a conventional method.

| Formulation: | |
|---|---|
| Compound (1p) of Example 7 | 1.0 (wt %) |
| Squalane | 2.0 |
| Octyldodecyl myristate | 3.0 |
| α-Isostearyl glyceryl ether | 2.0 |
| Dimethylpolysiloxane | 3.0 |
| Fine powder of titanium oxide | 3.0 |
| Butyl paraben | 0.2 |
| Glycerol | 10.0 |
| Magnesium sulfate | 1.0 |
| Methyl paraben | 0.3 |
| Purified water | Balance |

This cream provided excellent safety for the skin, and the UV shielding effect of the cream lasted a long time.

Example 16

A dual-phase anti-suntan emulsion having the following formulation was prepared according to a conventional method.

| Formulation: | |
|---|---|
| Compound (1v) of Example 10 | 5.0 (wt %) |
| Liquid paraffin | 10.0 |
| Squalane | 5.0 |
| Octamethyl cyclotetrasiloxane | 5.0 |
| Perfluoropolyether | 10.0 |
| Dimethylpolysiloxane-polyoxyalkylene copolymer | 1.0 |
| Glycerol | 2.0 |
| Ethanol | 5.0 |
| Zinc oxide | 7.5 |
| Octyl methoxycinnamate | 2.0 |
| Perfume | 0.01 |
| Purified water | Balance |

This emulsion provided excellent safety for the skin, and the UV shielding effect of the emulsion lasted a long time.

The disclosures of Japanese Patent Application Nos. HEI 5-143890 (1993) filed on Jun. 15, 1993 and HEI 6-057084 filed on Mar. 28, 1994 are incorporated herein by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A phosphoric diester having formula (1):

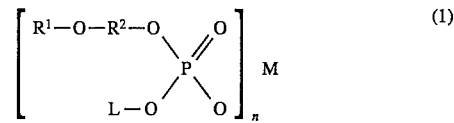

wherein $R^2$ is a $C_{2-12}$ linear or branched alkylene group or said alkylene group having an oxygen atom inserted between two carbon atoms thereof, L is a $C_{2-40}$ linear or branched alkylene group or said alkyl group having an oxygen atom inserted between two carbon atoms thereof or the group $R^1$-O-$R^2$-, M is a hydrogen atom, an alkali metal ion, a metal ion of di- or higher valence, an ammonium group, an alkanolammonium group having 2 to 14 carbon atoms, or a $C_{1-14}$ alkylammonium group, and n is the same number as the valence of M, wherein $R^1$ is a cinnamoyl group, a benzoyl group or said cinnamoyl group or benzoyl group substituted with an alkoxy, hydroxy, amino, alkylamino or dialkylamino group.

2. The phosphoric diester of claim 1, wherein $R^1$ is a p-methoxycinnamoyl group.

3. The phosphoric diester of claim 1, wherein $R^1$ is a benzoyl group.

4. The phosphoric diester of claim 1, wherein M is a calcium ion or an aluminum ion.

5. The phosphoric diester of claim 2, wherein M is a calcium ion or an aluminum ion.

6. The phosphoric diester of claim 3, wherein M is a calcium ion or an aluminum ion.

7. The phosphoric diester of claim 1, wherein L is a $C_{8-20}$ linear or branched alkyl group.

8. A cosmetic composition, comprising a phosphoric diester having formula (1):

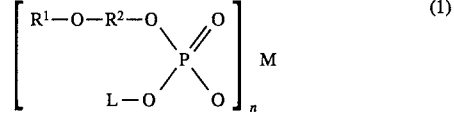

wherein $R^2$ is a $C_{2-12}$ linear or branched alkylene group or said alkylene group having an oxygen atom inserted between two carbon atoms thereof, L is a $C_{2-40}$ linear or branched alkylene group or said alkyl group having an oxygen atom inserted between two carbon atoms thereof or the group $R^1$-O-$R^2$-, M is a hydrogen atom, an alkali metal ion, a metal ion of di- or higher valence, an ammonium group, an alkanolammonium group having 2 to 14 carbon atoms, or $C_{1-14}$ alkylammonium group, n is the same number as the valence of M; and a cosmetic base, wherein $R^1$ is a cinnamoyl group, a benzoyl group or said cinnamoyl group or benzoyl group substituted with an alkoxy, hydroxy, amino, alkylamino or dialkylamino group.

9. The cosmetic composition of claim 8, wherein $R^1$ is a p-methoxycinnamoyl group.

10. The cosmetic composition of claim 8, wherein $R^1$ is a benzoyl group.

11. The cosmetic composition of claim 8, wherein M is a calcium ion or an aluminum ion.

12. The cosmetic composition of claim 9, wherein M is a calcium ion or an aluminum ion.

13. The cosmetic composition of claim 10, wherein M is a calcium ion or an aluminum ion.

14. The cosmetic composition of claim 8, further comprising an oil or an organic oil-based UV absorbing agent.

15. The cosmetic composition of claim 9, further comprising an oil or an organic oil-based UV absorbing agent.

16. The cosmetic composition of claim 10, further comprising an oil or an organic oil-based UV absorbing agent.

17. The cosmetic composition of claim 11, further comprising an oil or an organic oil-based UV absorbing agent.

18. The cosmetic composition of claim 12, further comprising an oil or an organic oil-based UV absorbing agent.

19. The cosmetic composition of claim 13, further comprising an oil or an organic oil-based UV absorbing agent.

* * * * *